(12) United States Patent
Matsunaga et al.

(10) Patent No.: US 8,548,578 B2
(45) Date of Patent: Oct. 1, 2013

(54) LIVING BODY STATE MONITOR APPARATUS

(75) Inventors: Shinya Matsunaga, Kariya (JP); Shinji Nanba, Kariya (JP); Tsuyoshi Nakagawa, Aichi-gun (JP); Kouki Futatsuyama, Anjo (JP); Takao Katoh, Tokyo (JP); Hiroshige Murata, Tokyo (JP); Hiroshi Hayashi, Tokyo (JP); Motohisa Osaka, Tokyo (JP); Minoru Makiguchi, Toyota (JP)

(73) Assignees: DENSO CORPORATION, Kariya (JP); Toyota Jidosha Kabushiki Kaisha, Toyota (JP); Nippon Medical School Foundation, Tokyo (JP)

( * ) Notice: Subject to any disclaimer, the term of this patent is extended or adjusted under 35 U.S.C. 154(b) by 55 days.

(21) Appl. No.: 13/272,282

(22) Filed: Oct. 13, 2011

(65) Prior Publication Data

US 2012/0095358 A1    Apr. 19, 2012

(30) Foreign Application Priority Data

Oct. 14, 2010    (JP) .................................. 2010-231725

(51) Int. Cl.
*A61B 5/00*    (2006.01)

(52) U.S. Cl.
USPC .......................................................... 600/513

(58) Field of Classification Search
USPC ................................................... 600/508–521
See application file for complete search history.

(56) References Cited

U.S. PATENT DOCUMENTS

| 6,095,984 A | 8/2000 | Amano et al. |
| 2001/0051773 A1 | 12/2001 | Oka |
| 2007/0265540 A1 | 11/2007 | Fuwamoto et al. |

*Primary Examiner* — Scott Getzow
(74) *Attorney, Agent, or Firm* — Posz Law Group, PLC

(57) ABSTRACT

A living body state monitor apparatus includes: a living body information acquisition device to acquire living body information containing an electrocardiography waveform and a pulse waveform from a user; an irregular heartbeat detection section to detect an irregular heartbeat from the electrocardiography waveform; and a pulse wave feature quantity extraction section to extract a pulse wave feature quantity from a pulse wave corresponding to the irregular heartbeat. Further, a living body state determination section is included to determine a danger degree on user's living body state using both of (A) information on kind and/or continued time period of an irregular heartbeat detected by the irregular heartbeat detection section, and (B) a pulse wave feature quantity extracted by the pulse wave feature quantity extraction section, and/or a variation of the extracted pulse wave feature quantity.

15 Claims, 13 Drawing Sheets

ELECTROCARDIOGRAPHY

PULSE WAVE

FIG. 12

| DANGER DEGREES OF PULSE WAVE FEATURE QUANTITIES | f1 | f2 | f3 | f4 | f5 |
|---|---|---|---|---|---|
| WEIGHTING FACTORS | α | β | γ | δ | ε |
| KINDS OF IRREGULAR HEARTBEAT | | | | | |
| VENTRICULAR FIBRILLATION | 0 | 1 | 0 | 0 | 0 |
| VENTRICULAR TACHYCARDIA | 1 | 0 | 0 | 0 | 0 |
| ATRIAL FIBRILLATION | 0.2 | 0 | 0.4 | 0.4 | 0 |
| ATRIAL FLUTTER/ TOP VENTRICULAR TACHYCARDIA | 0.2 | 0.8 | 0 | 0 | 0 |
| ATRIO-VENTRICULAR BLOCK/ SINUS ARREST | 0.2 | 0 | 0 | 0 | 0.8 |
| VENTRICULAR PREMATURE BEAT/ ATRIAL PREMATURE CONTRACTION | 0.5 | 0 | 0 | 0.5 | 0 |

US 8,548,578 B2

LIVING BODY STATE MONITOR APPARATUS

CROSS REFERENCE TO RELATED APPLICATION

The present application is based on and incorporates herein by reference Japanese Patent Application No. 2010-231725 filed on Oct. 14, 2010.

FIELD OF THE INVENTION

The present invention relates to a living body state monitor apparatus which monitors a living body state of a user.

BACKGROUND OF THE INVENTION

[Patent document 1] JP-2007-301101 A (US2007/0265540)
[Patent document 2] JP-2001-346769 A (US2001/0051773)

There is conventionally existing a system in a moving object such as a vehicle to measure an electrocardiography signal from a steering wheel to thereby determine an irregular heartbeat (i.e., arrhythmia) (refer to Patent document 1). This system measures an electrocardiography signal of "Lead I" from the both hands which grasp the steering wheel.

In addition, there is known a circulatory state monitor apparatus which can determine a patient's circulatory state with an irregular heartbeat detected from an electrocardiography, a pulse waveform resulting from pressure to a cuff, and a pulse waveform from a photoelectric sensor (refer to Patent document 2).

However, the conventional system is apt to be affected by the influence of the noise etc.; thus, it is not so easy to determine the danger on user's living body state accurately.

SUMMARY OF THE INVENTION

The present invention is made in view of the above problem. It is an object to provide a living body state monitor apparatus which can determine accurately a danger degree on user's living body state or living body information.

To achieve the above object, according to an aspect of the present invention, a living body state monitor apparatus is provided as follows. A living body information acquisition device is included to acquire living body information containing an electrocardiography waveform and a pulse waveform with respect to a living body of a user. An irregular heartbeat detection section is included to detect an irregular heartbeat from the electrocardiography waveform. A pulse wave feature quantity extraction section is included to extract a pulse wave feature quantity from a pulse wave corresponding to the irregular heartbeat. A living body state determination section is included to determine a danger degree on living body state of the user using two of: (i) information on kind and/or time of an irregular heartbeat detected by the irregular heartbeat detection section; and (ii) a pulse wave feature quantity extracted by the pulse wave feature quantity extraction section, and/or a variation of the extracted pulse wave feature quantity.

Under the above configuration, a danger degree on driver's living body state is determined comprehensively using not only the electrocardiography waveform but also the pulse wave. The danger degree on driver's living body state can be thus determined correctly even in cases where an irregular heartbeat which does not exist actually is mistakenly detected, or an anomaly on pulse wave which does not exist actually is mistakenly detected.

BRIEF DESCRIPTION OF THE DRAWINGS

The above and other objects, features, and advantages of the present invention will become more apparent from the following detailed description made with reference to the accompanying drawings. In the drawings:

FIG. 12 is a diagram for explaining weighting factors for calculating a pulse wave danger degree;

DETAILED DESCRIPTION OF THE PREFERRED EMBODIMENTS

The following describes embodiments of the present invention with reference to drawings.

First Embodiment

1. Configuration of Living Body State Monitor Apparatus 1

Figure 1:
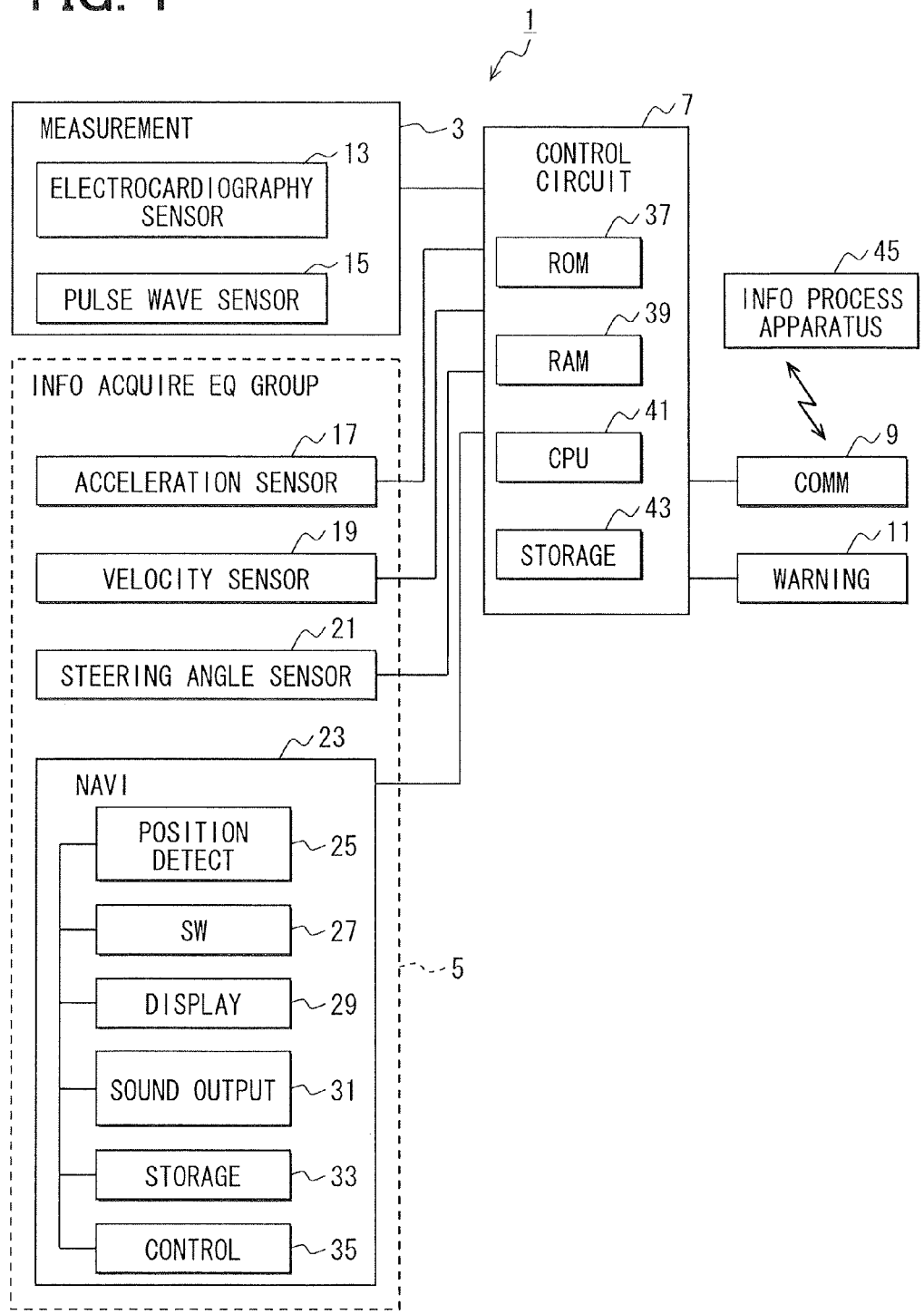
FIG. 1 is a block diagram illustrating a schematic configuration of a living body state monitor apparatus and peripheral equipment according to an embodiment of the present invention.
Figure 2:
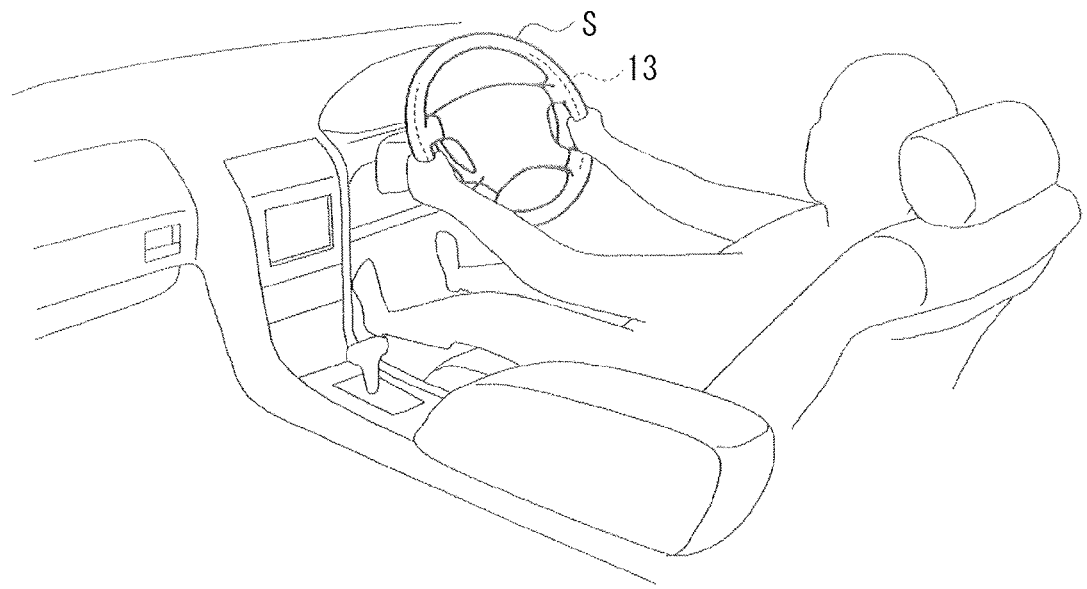
FIG. 2 is a diagram for explaining a measurement device provided in a vehicular compartment of a vehicle.
Figure 3:
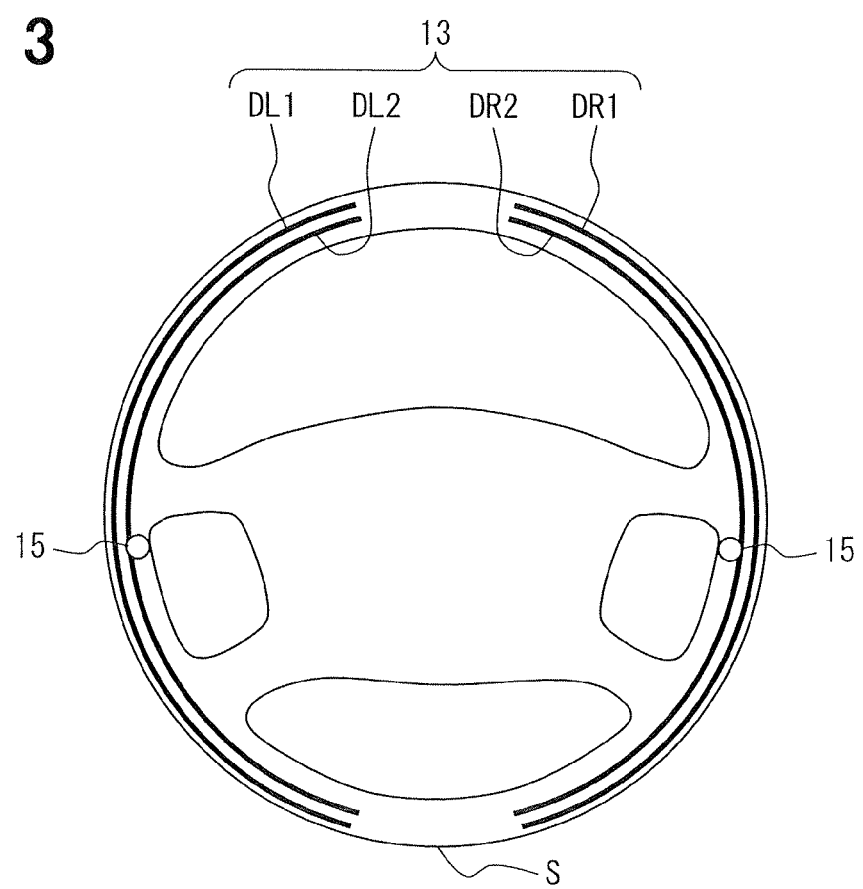
FIG. 3 is a diagram for explaining the measurement device arranged in a steering wheel of the vehicle.
Figure 4:
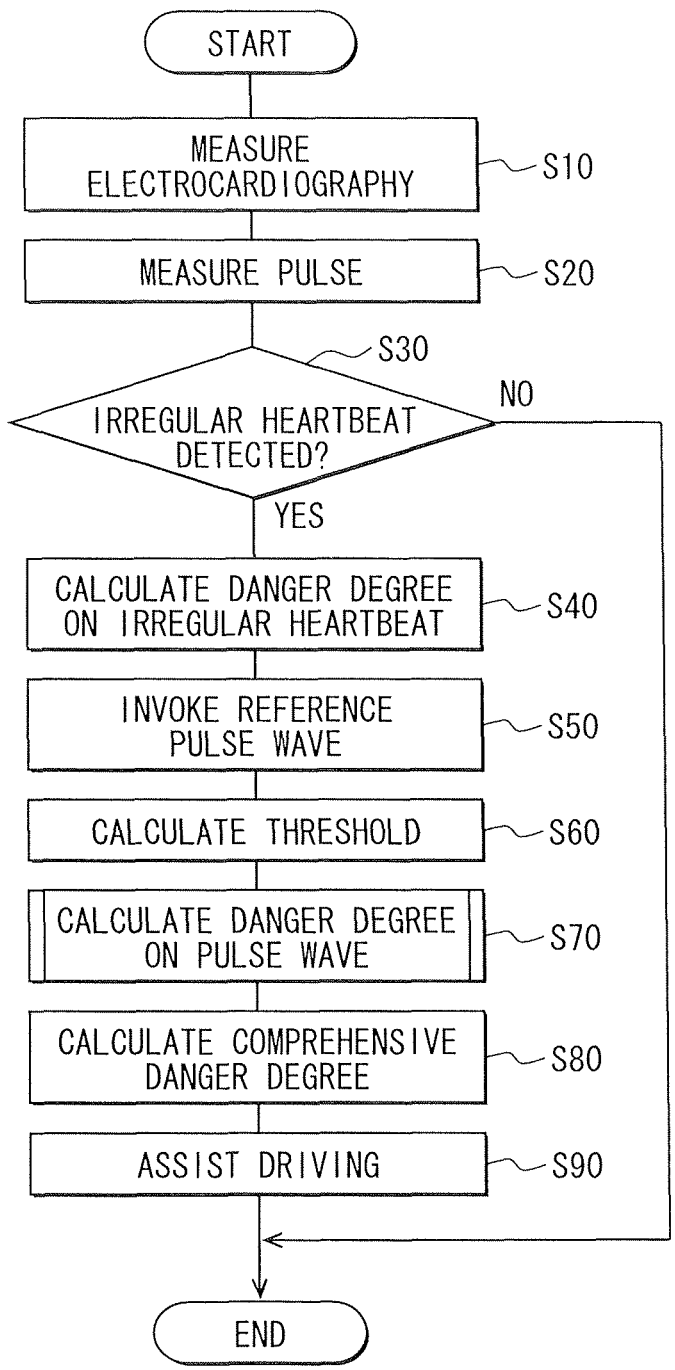
FIG. 4 is a flowchart diagram illustrating a process executed by the living body state monitor apparatus.
Figure 5:
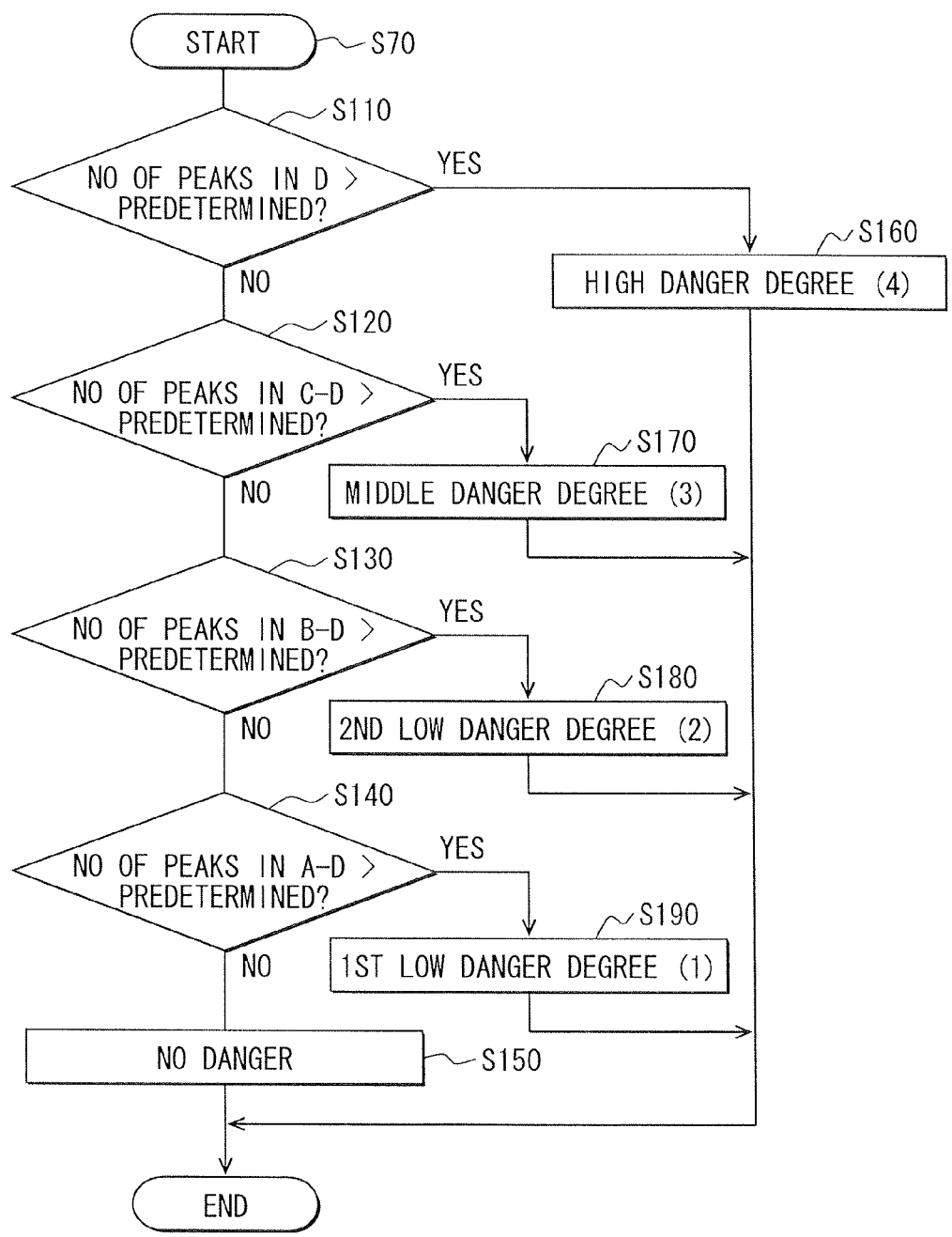
FIG. 5 is a flowchart diagram illustrating a process to calculate a pulse wave danger degree.

Based on FIGS. 1 to 3, a configuration of a living body state monitor apparatus 1 will be explained. FIG. 1 is a block diagram illustrating a schematic configuration of a living body state monitor apparatus 1 mounted in a subject vehicle and its peripheral equipment. FIG. 2 is a diagram for explaining a measurement device 3 arranged in a vehicular compartment of the subject vehicle. FIG. 2 is a diagram for explaining the measurement device 3 arranged in a steering wheel S of the subject vehicle.

The living body state monitor apparatus 1 includes the following: a measurement device 3 (i.e., a living body information acquisition device 3) which acquires living body information that contains an electrocardiography waveform and a pulse wave from a driver (i.e., a living body of the driver) of the subject vehicle; an information acquisition equipment group 5 (i.e., a driving information acquisition device 5) which acquires a variety of information containing an acceleration applied to the subject vehicle; a control circuit which executes processes to be mentioned later using the information acquired by the measurement device 3 and/or the information acquisition equipment group 5; a communication device 9, which also functions as an output device, for executing data communications via a public communication link or network; and a warning device 11, which also functions as an assistance device for warning in the subject vehicle. The control circuit 7 may be also referred to or function as an irregular heartbeat detection section, a pulse wave feature quantity extraction section, a living body state determination section.

The measurement device 3 includes an electrocardiography sensor 13 which measures an electrocardiography waveform, and a pulse wave sensor 15 which measures a pulse wave. As indicated in FIG. 2 and FIG. 3, the electrocardiography sensor 13 includes two pairs of electrodes provided in a steering wheel S of the subject vehicle. The one pair of electrodes DR1, DR2 are arranged in a portion gripped by a right hand; the other pair of electrodes DL1, DL2 are arranged in a portion gripped by a left hand. The electrocardiography sensor 13 uses the two pairs of electrodes DR1, DR2, DL1, DL2, as a sensing electrode device to measure an electrocardiography waveform. In addition, the pulse wave sensor 15 includes an optical volume pulse wave instrument arranged in the steering wheel S to measure a pulse wave. The volume pulse wave instrument is built in a portion which a palm contacts in the steering wheel S to optically detect a volumetric change in a blood vessel. That is, the measurement device 3 measures as living body information an electrocardiography waveform and a pulse wave, and outputs a result of the measurement (i.e., a sampling value) to the control circuit 7.

The information acquisition equipment group 5 includes an acceleration sensor 17 which detects an acceleration applied to the subject vehicle, a velocity sensor 19 which detects a velocity of the subject vehicle, a steering angle sensor 21 which detects an angle of the steering wheel S of the subject vehicle, and a navigation apparatus 23 which acquires a present position of the subject vehicle and provides a guidance of a estimated travel route of the subject vehicle.

The acceleration sensor 17 is a known three-axial acceleration sensor which detects an acceleration applied to the subject vehicle in each of three directions (i.e., a longitudinal (vehicle-length) direction, a lateral (vehicle-width) direction, and a vertical (vehicle-height) direction. In addition, the navigation apparatus 23 includes the following: a position detection device 25 to detect a present position of the subject vehicle; a manipulation switch group 27 to receive a variety of instructions by a user; a display device 29 to display various images; and a sound output device to output various kinds of guidance sounds, for example. In addition, the navigation apparatus 23 includes a storage device 33 to store the various data such as map data, and a control circuit 35. The control circuit 35 controls constitutional devices of the navigation apparatus 23 such as the storage device 33, the display device 29, and the sound output device 31, according to an input signal from the position detection device 25 and/or the manipulation switch group 27.

The position detection device 25 includes the following known sensors or the like (none shown): a GPS receiver, which receives via a GPS antenna (not shown) electric waves from satellites for GPS (Global Positioning System) and outputs reception signals; a gyro sensor which detects rotational movement exerted over the subject vehicle; and an electromagnetic sensor which detects a travel direction from the electromagnetism.

Furthermore, the control circuit 7 mainly includes a well-known microcomputer. The microcomputer has the following: a ROM 37 storing data whose memory contents need to be held even if a power source is disconnected; a RAM 39 storing data temporarily; a CPU 41 executing a process according to a program stored in the ROM 37 or RAM 39; and a bus interconnecting the foregoing. The microcomputer is connected with a rewritable non-volatile storage device 43 such as a hard disk drive, an EEPROM, or a flash memory. The ROM 37 stores a processing program for executing processes mentioned later. The control circuit 7 functions as a living body state determination section or means.

The communication device 9 executes information communications with an information processing apparatus 45, which is arranged in an external medical institution separate from the subject vehicle, via a general communication link or network (e.g., a wireless communication link) according to instructions from the control circuit 7. It is noted that the information processing apparatus 45 includes at least a communication device (not shown) which receives information transmitted from the communication device 9, and a known information processing unit (not shown), which has a function to store the information received by the communication device and process the received information.

2. Process by Living Body State Monitor Apparatus 1

The processes which the living body state monitor apparatus 1 (in particular, the control circuit 7) executes are explained with reference to FIGS. 4 to 8. These processes are started when an ignition signal of the subject vehicle is inputted into the living body state monitor apparatus 1, and, further, executed repeatedly every predetermined time interval.

It is further noted that a flowchart or the processing of the flowchart in the present application includes sections (also referred to as steps), which are represented, for instance, as S10. Further, each section can be divided into several subsections while several sections can be combined into a single section. Furthermore, each of thus configured sections can be referred to as a device, means, module, or processor and achieved not only as a software section in combination with a hardware device but also as a hardware section. Furthermore, the software section may be included in a software program, which may be contained in a non-transitory computer-readable storage media as a program product.

Figure 6A:
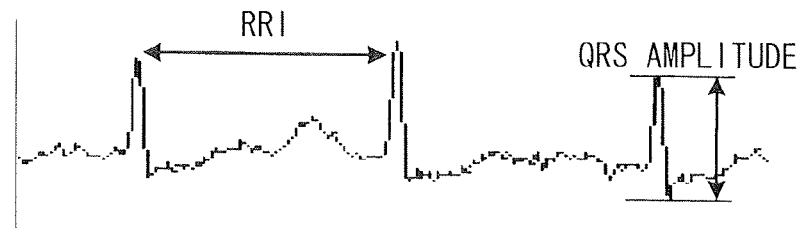
FIGS. 6A, 6B are diagrams for explaining an electrocardiography waveform and a pulse wave.

At S10, an electrocardiography waveform is acquired from a driver of the subject vehicle by the electrocardiography sensor 13. The acquired electrocardiography waveform is outputted to the control circuit 7. An example of the acquired electrocardiography waveform is indicated in FIG. 6A.

Figure 6B:
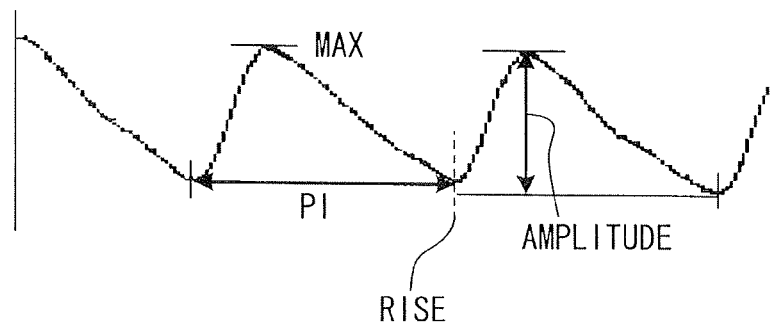

At S20, a pulse waveform is acquired from the driver of the subject vehicle by the pulse wave sensor 15. The acquired pulse waveform is outputted to the control circuit 7. An example of the acquired pulse waveform is indicated in FIG. 6B.

At S30, it is determined whether an irregular heartbeat is detected in the electrocardiography waveform acquired at S10. The following explains in detail. An electrocardiography feature quantity is extracted from the electrocardiography waveform acquired at S10. The electrocardiography feature quantity includes RRI (Interval between an R wave and the next R wave), HR, QRS width, and QRS amplitude. RRI and QRS amplitude are indicated in FIG. 6A. Presence or absence of an irregular heartbeat and a kind (i.e., classification) of the irregular heartbeat are determined from the extracted electrocardiography feature quantity. The irregular heartbeat includes several kinds or classifications of ventricular fibrillation, ventricular tachycardia, atrial fibrillation, atrial flutter, top ventricular tachycardia, atrio-ventricular block, sinus arrest, ventricular premature beat, and atrial premature contraction. Since there is a predetermined constant association between an electrocardiography feature quantity and a kind of the irregular heartbeat can be determined from the electrocardiography feature quantity. The living body state monitor apparatus 1 previously stores a map which stipulates an association between a value of an electrocardiography feature quantity, and a kind of the irregular heartbeat. The kind of the irregular heartbeat can be determined by applying the electrocardiography feature quantity to the map. When an irregular heartbeat is detected, the processing proceeds to S40. When it is not detected, the present process is ended.

At S40, a danger degree (in lethality) of the irregular heartbeat detected at S30 is calculated. The following explains in detail. First, the kind of the irregular heartbeat determined at S30 is acquired. Next, the length (also referred to as a time, a duration, a time period, or information on time) of the irregular heartbeat is acquired from the electrocardiography waveform acquired at S10. Finally, the danger degree of the irregular heartbeat (also referred to as a danger degree on irregular heartbeat, or an irregular heartbeat danger degree) is determined from the kind and length of the irregular heartbeat. It is noted that the living body state monitor apparatus 1 previously stores a map which stipulates an association between a kind and length of an irregular heartbeat and a danger degree of the irregular heartbeat. The danger degree of the irregular heartbeat can be determined by applying the kind and length of the irregular heartbeat, which were found as mentioned above, to the map. When an irregular heartbeat appears, the appearing irregular heartbeat is always compared with records of irregular heartbeats having appeared within a past predetermined time period just before the irregular heartbeat appearing. When an appearance frequency of the sporadic irregular heartbeats increases, such increase of the frequency is considered as a factor which should be added to the danger degree.

At S50, a reference pulse wave is invoked. This reference pulse wave is an average waveform of several pulse waveforms acquired in a predetermined past time period and stored in the storage device 43 (refer to FIG. 1).

Figure 7:
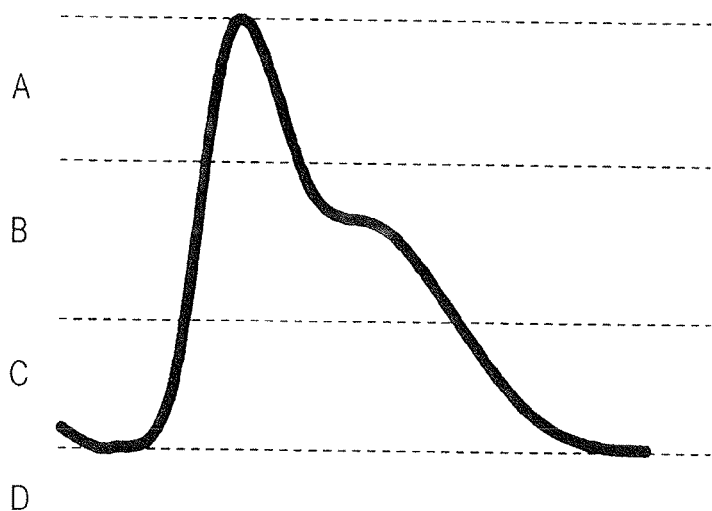
FIG. 7 is a diagram for explaining a method to calculate a threshold value using a reference pulse wave.

At S60, a threshold value is calculated using the reference pulse wave invoked at S50. This is explained with reference to FIG. 7. The waveform indicated in FIG. 7 is a reference pulse wave invoked at S50. An interval between the maximum value and the minimum value in a single reference pulse wave is equally divided into three segments A, B, C in order from the maximum value. In addition, a segment below the minimum value is defined as a segment D.

At S70, a danger degree on pulse wave (also referred to as a pulse wave danger degree) is calculated. This is explained with reference to a flowchart in FIG. 5. At S110, a reference pulse wave (i.e., one-peak reference pulse wave) is compared with a pulse wave corresponding to the irregular heartbeat within the pulse waveform acquired at S20 in respect of a maximum value of a peak. The pulse wave corresponding to the irregular heartbeat is a part of the pulse waveform within a predetermined time period just after the onset of the irregular heartbeat occurring or corresponding to a predetermined number of peaks (i.e., beats) after the onset of the irregular heartbeat. As a result, when the number of peaks having maximum values present in the segment D is greater than a predetermined number, it is determined at S160 that the danger degree belongs to a high danger degree (the danger degree highest among the five levels). The present process is then ended. In contrast, when the above condition is not satisfied, the processing proceeds to S120.

At S120, the above reference pulse wave is compared with the pulse wave corresponding to the irregular heartbeat within the pulse waveform acquired at S20 in respect of a maximum value of a peak. As a result, when the number of peaks having maximum values present in the segments C and D is greater than a predetermined number, it is determined at S170 that the danger degree belongs to a middle danger degree (the danger degree second highest among the five levels). The present process is then ended. In contrast, when the above condition is not satisfied, the processing proceeds to S130.

At S130, the above reference pulse wave is compared with the pulse wave corresponding to the irregular heartbeat within the pulse waveform acquired at S20 in respect of a maximum value of a peak. As a result, when the number of peaks having maximum values present in the segments B, C, and D is greater than a predetermined number, it is determined at S180 that the danger degree belongs to a second low danger degree (the danger degree third highest among the five levels). The present process is then ended. In contrast, when the above condition is not satisfied, the processing proceeds to S140.

At S140, the above reference pulse wave is compared with the pulse wave corresponding to the irregular heartbeat within the pulse waveform acquired at S20 in respect of a maximum value of a peak. As a result, when the number of peaks having maximum values present in the segments A, B, C, and D is greater than a predetermined number, it is determined at S190 that the danger degree belongs to a first low danger degree (the danger degree fourth highest among the five levels). The present process is then ended. In contrast, when the above condition is not satisfied, the processing proceeds to S150. At S150, it is determined that there is no danger (the danger degree lowest among the five levels). The present process is then ended.

Figure 8:
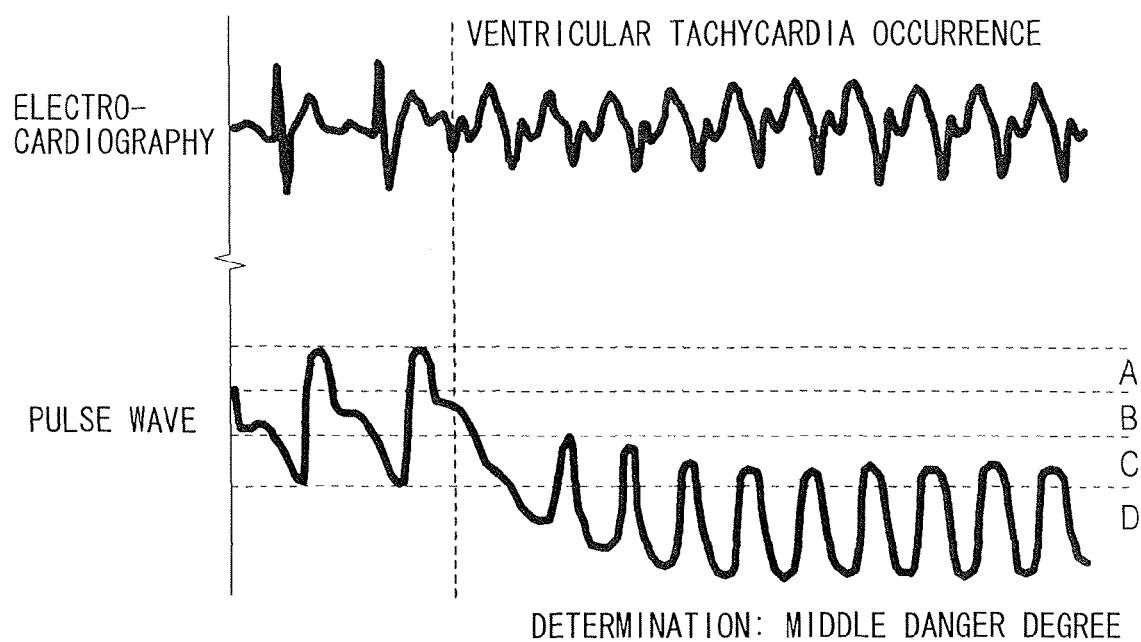
FIG. 8 is a diagram for explaining a method to determine a danger degree in a pulse wave.

An example which determines that the danger degree on pulse wave is a middle danger degree is indicated in FIG. 8. In the pulse wave corresponding to the irregular pulses, all the maximum values of the peaks are all in the segments C and D. Returning to FIG. 4, at S80, a comprehensive danger degree on pulse wave is calculated. This comprehensive danger degree is obtained by comprehensively combining the danger degree on irregular heartbeat calculated at S40 and the danger degree on pulse wave calculated at S70. For example, the comprehensive danger degree can be obtained by adding up a point calculated based on the danger degree on irregular heartbeat, and a point calculated based on the danger degree on pulse wave.

At S90, a driving operation assistance is executed based on the comprehensive danger degree calculated at S80. For example, when the comprehensive danger degree is positioned at the highest level, a signal is outputted to an external source from the communication device 9. The outputted signal may include an electrocardiography waveform, a pulse waveform, a comprehensive danger degree, an identification number of the driver or the subject vehicle, for instance. In addition, when the comprehensive danger is lower than the highest level, a warning may be executed in a vehicle compartment of the subject vehicle using the display device 29 or the sound output device 31. This warning is more conspicuous as the comprehensive danger degree becomes higher. In addition, when the comprehensive danger degree does not exist or when the comprehensive danger degree is less than a predetermined value, a driving operation assistance is not executed.

3. Effect by Living Body State Monitor Apparatus 1

(1) The living body state monitor apparatus 1 determines a danger degree on driver's living body state comprehensively not only using the electrocardiography waveform but also using the pulse waveform. The danger degree on driver's living body state can be thus determined correctly even in cases where an irregular heartbeat which does not exist actually is mistakenly detected because of vibration of the subject vehicle, driver's body movement, or electromagnetic waves, for instance, or an anomaly on pulse wave which does not exist actually is mistakenly detected.

Figure 9:
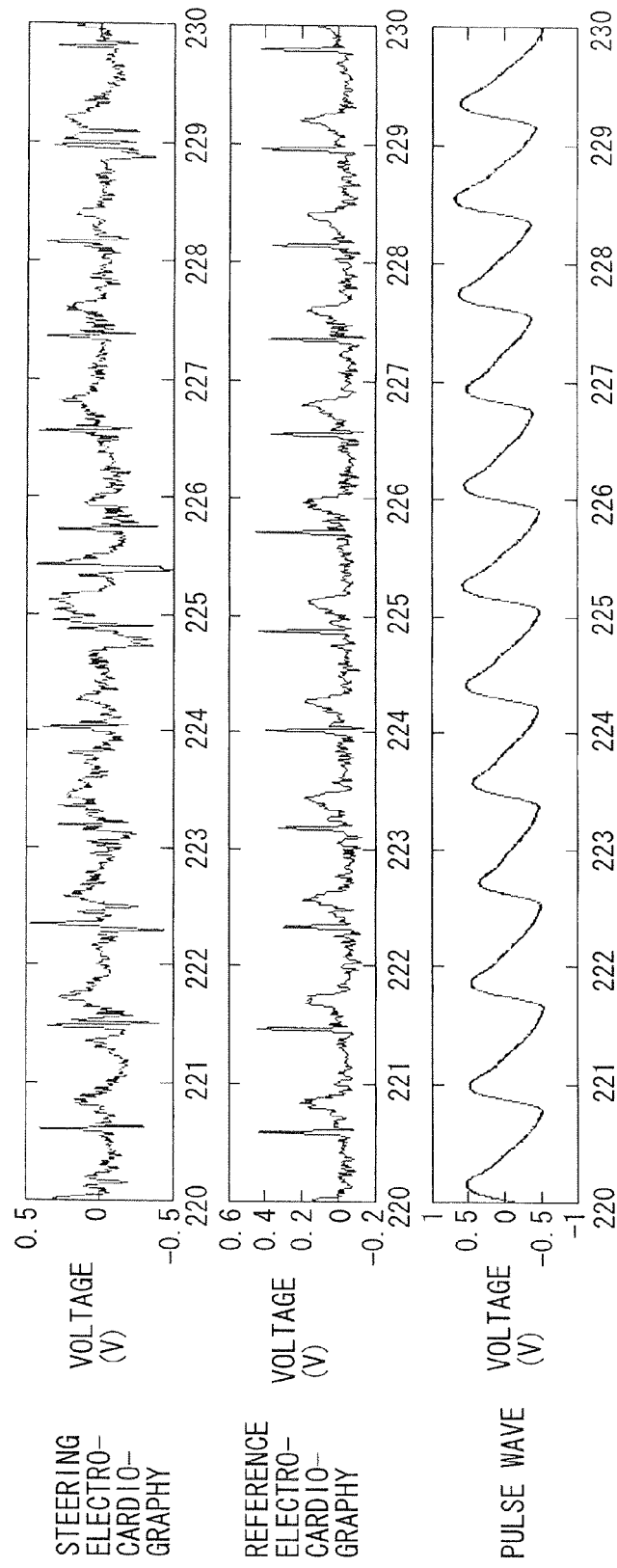
FIG. 9 is a diagram of an example, which illustrates an electrocardiography waveform of a steering wheel electrocardiography indicating an irregular heartbeat, a reference electrocardiography indicating no anomaly, and a pulse wave indicating no anomaly.
Figure 10:
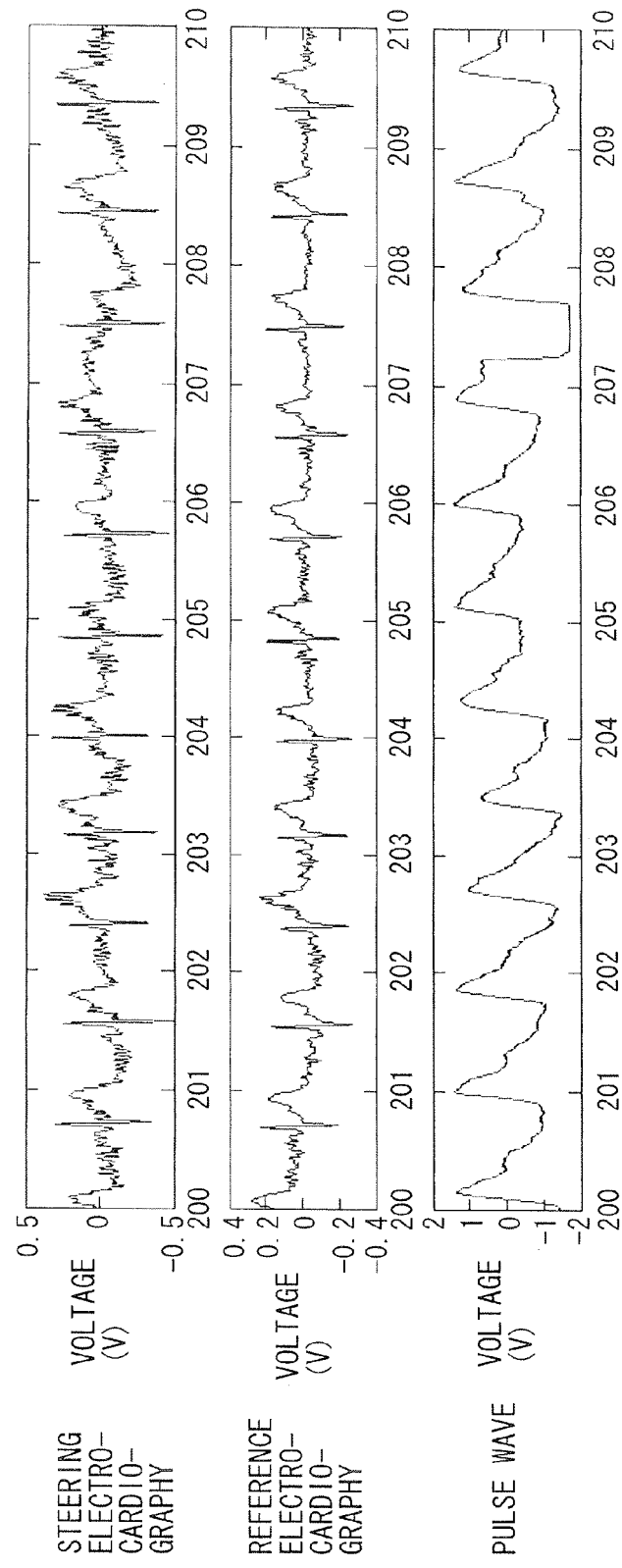
FIG. 10 is a diagram of an example, which illustrates an electrocardiography waveform of a steering wheel electrocardiography indicating no irregular heartbeat, a reference electrocardiography indicating no irregular heartbeat, and a pulse wave indicating an anomaly.

It is noted that the above effect is supported with the following data. FIG. 9 and FIG. 10 indicate results about an identical test subject of acquiring simultaneously a steering wheel electrocardiography, which is an electrocardiography waveform by the electrocardiography sensor 13, a reference electrocardiography, which is an electrocardiography waveform by an electrocardiograph of a medical use, and a pulse waveform by the pulse wave sensor 15.

In FIG. 9, an electrocardiography waveform of the steering wheel electrocardiography indicates an irregular heartbeat, while a reference electrocardiography indicates no anomaly, and a pulse waveform indicates no anomaly. This case indicates an incorrect detection of an irregular heartbeat by the electrocardiography sensor 13. If a danger degree on driver's living body state is determined only based on the steering wheel electrocardiography, there may be a problem that the danger degree is incorrectly determined because of the irregular heartbeat which is mistakenly detected. In contrast, according to the living body state monitor apparatus 1 of the present embodiment, the danger degree on driver's living body state is comprehensively determined using both the electrocardiography waveform and the pulse waveform; thus, the above problem does not arise.

In FIG. 10, while an electrocardiography waveform of a steering wheel electrocardiography indicates no irregular heartbeat and a reference electrocardiography indicates no irregular heartbeat, a pulse wave indicates an anomaly. This case indicates an incorrect detection of an anomaly on pulse wave by the pulse wave sensor 15. If a danger degree on driver's living body state is determined only based on the pulse waveform, the danger degree is incorrectly determined because of the anomaly on pulse wave which is mistakenly detected. In contrast, according to the living body state monitor apparatus 1 of the present embodiment, the danger degree on driver's living body state is comprehensively determined using both the electrocardiography waveform and the pulse waveform; thus, the above problem does not arise.

(2) The living body state monitor apparatus 1 can determine a danger degree of the living body state.

Second Embodiment

The living body state monitor apparatus 1 in a second embodiment has a configuration similar to that of the first embodiment; processes to be executed are partially different from those of the first embodiment. Thus the following mainly explains such a different point while explanation of the same portion as that of the first embodiment is omitted or simplified.

Figure 11:
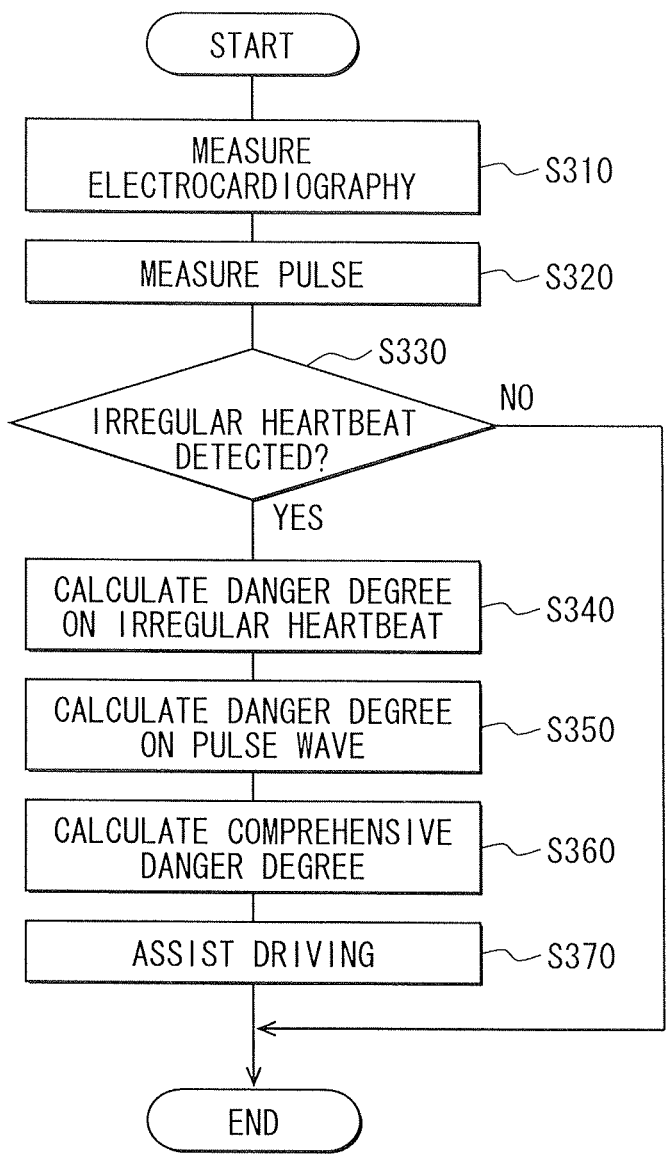
FIG. 11 is a flowchart diagram illustrating a process executed by the living body state monitor apparatus.

The process which the living body state monitor apparatus 1 (in particular, the control circuit 7) executes is explained with reference to FIG. 11. The process is started when an ignition signal of the subject vehicle is inputted into the living body state monitor apparatus 1, and, further, executed repeatedly every predetermined time interval.

S310 to S340 are the same as S10 to S40 in the first embodiment, respectively. At S350, a danger degree of a pulse wave corresponding to an irregular heartbeat is calculated. The danger degree pul(x) on pulse wave is expressed by the following formula (I).

$$\text{pul}(x) = \alpha \times f1(x) + \beta \times f2(x) + \gamma \times f3(x) + \delta \times f4(x) + \epsilon \times f5(x). \quad \text{Formula (1)}$$

Herein, $\alpha$, $\beta$, $\gamma$, $\delta$, and $\epsilon$ are weighting factors determined according to a kind of an irregular heartbeat determined at S330 as indicated in FIG. 12. For example, when the kind of the irregular heartbeat is ventricular fibrillation, $\beta=1$ and $\alpha=\gamma=\delta=\epsilon=0$. For example, when the kind of the irregular heartbeat is ventricular tachycardia, $\alpha=1$ and $\beta=\gamma=\delta=\epsilon=0$.

In addition, $f1(x)$, $f2(x)$, $f3(x)$, $f4(x)$, and $f5(x)$ are danger degrees calculated for the five kinds of pulse wave feature quantities, respectively. The following explains in detail.

$f1(x)$: a danger degree calculated from "the maximum value of one peak" (the maximum value of a pulse wave of one peak corresponding to an irregular heartbeat), which is a pulse wave feature quantity. As this pulse wave feature quantity is smaller than a threshold value, the danger degree becomes higher.

$f2(x)$: a danger degree calculated from "the amplitude of one peak" (the amplitude of a pulse wave of one peak corresponding to an irregular heartbeat), which is a pulse wave feature quantity. As this pulse wave feature quantity is smaller than a threshold value, the danger degree becomes higher.

$f3(x)$: a danger degree calculated from "the amplitudes for peaks the number of which is a predetermined number" (the variance of the amplitudes of the predetermined-number peaks of the pulse wave corresponding to an irregular heartbeat), which is a pulse wave feature quantity. As this pulse wave feature quantity is larger than a threshold value, the danger degree becomes higher.

$f4(x)$: a danger degree calculated from "the variation of PIs (Pulse Intervals) for peaks the number of which is a predetermined number" (the variance of PIs of the pulse wave covering predetermined peaks corresponding to an irregular heartbeat), which is a pulse wave feature quantity. The above predetermined peaks may be peaks the number of which is a predetermined number or may be existing within a predetermined time period. As this pulse wave feature quantity is larger than a threshold value, the danger degree becomes higher.

$f5(x)$: a danger degree calculated from "the PI (Pulse Interval) for one peak" (the PI of the pulse wave of one peak corresponding to an irregular heartbeat), which is a pulse wave feature quantity. As this pulse wave feature quantity is larger than a threshold value, the danger degree becomes higher. The following are examples of the kinds of the irregular heartbeat, the electrocardiography changes and the pulse wave changes, and the criteria for determining an irregular heartbeat, which are described in FIG. 12.

Ventricular premature beat (VPC), Atrial premature contraction (APC) Electrocardiography change: QRS wave occurs earlier than expected. Pulse wave change:
(1) The rise of the corresponding pulse wave becomes early.
(2) The maximum value of the corresponding pulse wave falls. Criteria:
(1) PI (Pulse Interval) is shorter than a threshold value. The PI is defined as a time period between (i) a first rise of a pulse wave corresponding to the irregular heartbeat and (ii) a second rise preceding the first rise by one peak.

(2) The maximum value of the corresponding pulse wave becomes less than a threshold value. ((1) and (2) may be separate or may be combined)

Ventricular tachycardia (VT)

Electrocardiography change: QRS waves arise consecutively earlier than expected.

Pulse wave change: With onset, the wave height of the pulse wave decreases; with continuity, the extent becomes stronger.

Criteria: The maximum values of the peaks of the corresponding pulse wave are consecutively less than a threshold value (i) for a predetermined time period or longer or (ii) by predetermined repetition times or more.

Ventricular fibrillation (VF)

Electrocardiography change: It exhibits completely irregular amplitudes/waveforms (QRS or T is not determined).

Pulse wave change: The peaks of the pulse wave become almost flat immediately after an onset of the irregular heartbeat.

Criteria: The amplitudes of the peaks of the pulse wave are less than a threshold value (i) for more than a predetermined time period immediately after detecting VF or (ii) up to a predetermined time after detecting VF.

Atrial fibrillation (AF)

Electrocardiography change: RRIs become uneven.

Pulse wave change: The wave heights and/or amplitudes of peaks of the pulse wave become disparate.

Criteria:

(1) The variance of PIs within a predetermined time period from the peak of the pulse wave immediately after detecting AF is greater than a predetermined threshold value.

(2) The variance of pulse wave amplitudes within a predetermined time period from the peak of the pulse wave immediately after detecting AF is greater than a predetermined threshold value. ((1) and (2) may be separate or may be combined.)

Atrial flutter, Top ventricular tachycardia

Electrocardiography change: The heart rate is fast.

Pulse wave change: Amplitudes become small even if the wave heights of the peaks of the pulse wave seldom change.

Criteria: Corresponding pulse wave amplitudes the number of which is a predetermined number are continuously less than a threshold value.

Atrio-ventricular block, Sinus arrest

Electrocardiography change: RRI extends since QRS wave does not occur locally (pauses or stops).

Pulse wave change: The peak of the pulse wave is missing in accordance with the length of the pause.

Criteria: The time period (PI: Pulse Interval) from the rise of the peak of the pulse wave before a pause up to the rise of the peak of the pulse wave after the pause is longer than a threshold value.

As mentioned above, at S350, the pulse wave feature quantity and determination method, which are used for determining a danger degree on pulse wave, are changed according to the kinds of the irregular heartbeat. S360 to S370 are the same as S80 to S90 in the first embodiment, respectively.

According to the living body state monitor apparatus 1 of the second embodiment, the pulse wave feature quantity and determination method, which are used for determining a danger degree on pulse wave, are changed according to the kinds of the irregular heartbeat. Thus, the danger degree on driver's living body state can be determined correctly regardless of the kinds of the irregular heartbeat.

Third Embodiment

The living body state monitor apparatus 1 in a third embodiment has a configuration similar to that of the first embodiment; a process to be executed is partially different from that of the first embodiment. Thus the following mainly explains such a different point while explanation of the same portion as that of the first embodiment is omitted or simplified.

Figure 13:
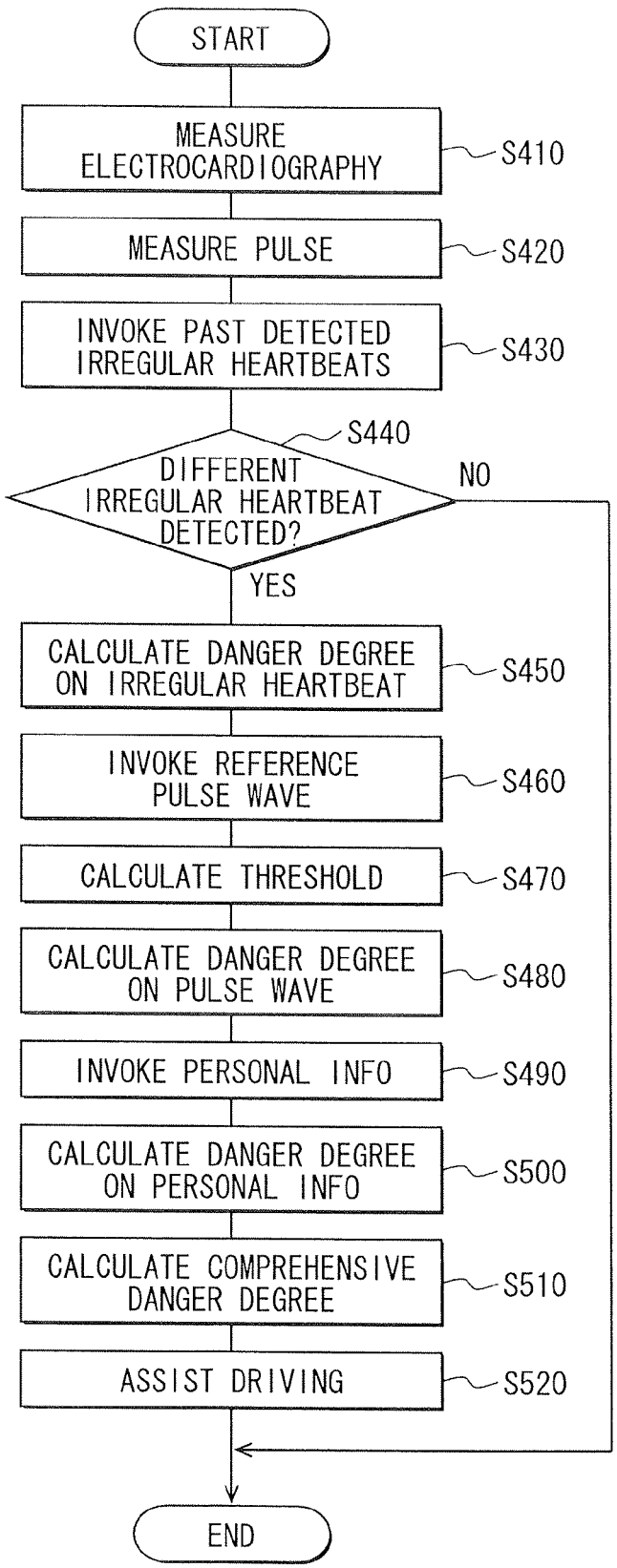
FIG. 13 is a flowchart diagram illustrating a process executed by the living body state monitor apparatus.

The process which the living body state monitor apparatus 1 (in particular, the control circuit 7) executes is explained with reference to FIG. 13. The process is started when an ignition signal of the subject vehicle is inputted into the living body state monitor apparatus 1, and, further, executed repeatedly every predetermined time interval.

S410 to S420 are the same as S10 to S20 in the first embodiment, respectively. At S430, an irregular heartbeat or irregular heartbeats are invoked which were detected within a past predetermined time period and then stored in the storage device 43. The storage device 43 stores or records the irregular heartbeats and the pulse wave feature quantities which were detected within the past predetermined time period; thus, it functions as a living body information storage device or means.

At S440, it is determined whether an irregular heartbeat is detected in the electrocardiography waveform acquired at S410. The method is the same as that of S330 in the second embodiment. Next, when the irregular heartbeat is detected, it is determined whether its kind is the same as one of the kinds of the irregular heartbeats invoked at S430. When the irregular heartbeat is detected and the kind of the irregular heartbeat differs from those of the irregular heartbeats invoked at S430, the processing proceeds to S450. In contrast, when the irregular heartbeat is not detected, or when the kind of the detected irregular heartbeat is the same as one of those of the irregular heartbeats invoked at S430, the present process is ended.

S450 to S480 are the same as S40 to S70 in the first embodiment, respectively. At S490, personal information previously stored in the storage device 43 is invoked. This personal information is previously inputted for each individual, or is information on irregular heartbeat or illness that was detected in the past. Thus, the storage device 43 also functions as a personal information storage device or means.

At S500, a danger degree is calculated using the personal information invoked at S490. For example, there may be a case where the irregular heartbeat determined at S450 corresponds to the previous illness recorded in the personal information, and the previous illness is estimated to become worse from the detection of the irregular heartbeat. In such a case, the danger degree resulting from the personal information is calculated to be high. In contrast, when the irregular heartbeat determined at S450 is not related to the previous illness recorded in the personal information, the danger degree resulting from the personal information is calculated to be lower than that of the preceding case.

At S510, a comprehensive danger degree is calculated. This comprehensive danger degree is obtained by comprehensively combining the danger degree on irregular heartbeat calculated at S450, the danger degree on pulse wave calculated at S480, and the danger degree from personal information calculated at S500. For example, the comprehensive danger degree can be obtained by adding up a point calculated based on the danger degree on irregular heartbeat, a point calculated based on the danger degree on pulse wave, and a point calculated based on the danger degree from personal information.

At S520, a driving operation assistance is executed based on the comprehensive danger degree calculated at S510. The driving operation assistance is the same as S90 in the first embodiment. In the living body state monitor apparatus 1 of the present embodiment, when the danger degree is determined to be relatively low as the result of S430, S440 (i.e., when the kind of the detected irregular heartbeat is the same as one of the kinds of the irregular heartbeats arising in the past), subsequent processing is omitted. This can provide an efficient process; the driver is not bothered by the unnecessary process, either.

In addition, according to the living body state monitor apparatus 1 of the present embodiment, the personal information is taken into consideration based on S490 to S500, enabling the more correct determination of the danger degree on driver's living body state.

Fourth Embodiment

The living body state monitor apparatus 1 in a fourth embodiment has a configuration similar to that of the first embodiment; a process to be executed is partially different from those of the first embodiment. Thus the following mainly explains such a different point while explanation of the same portion as that of the first embodiment is omitted or simplified.

Figure 14:
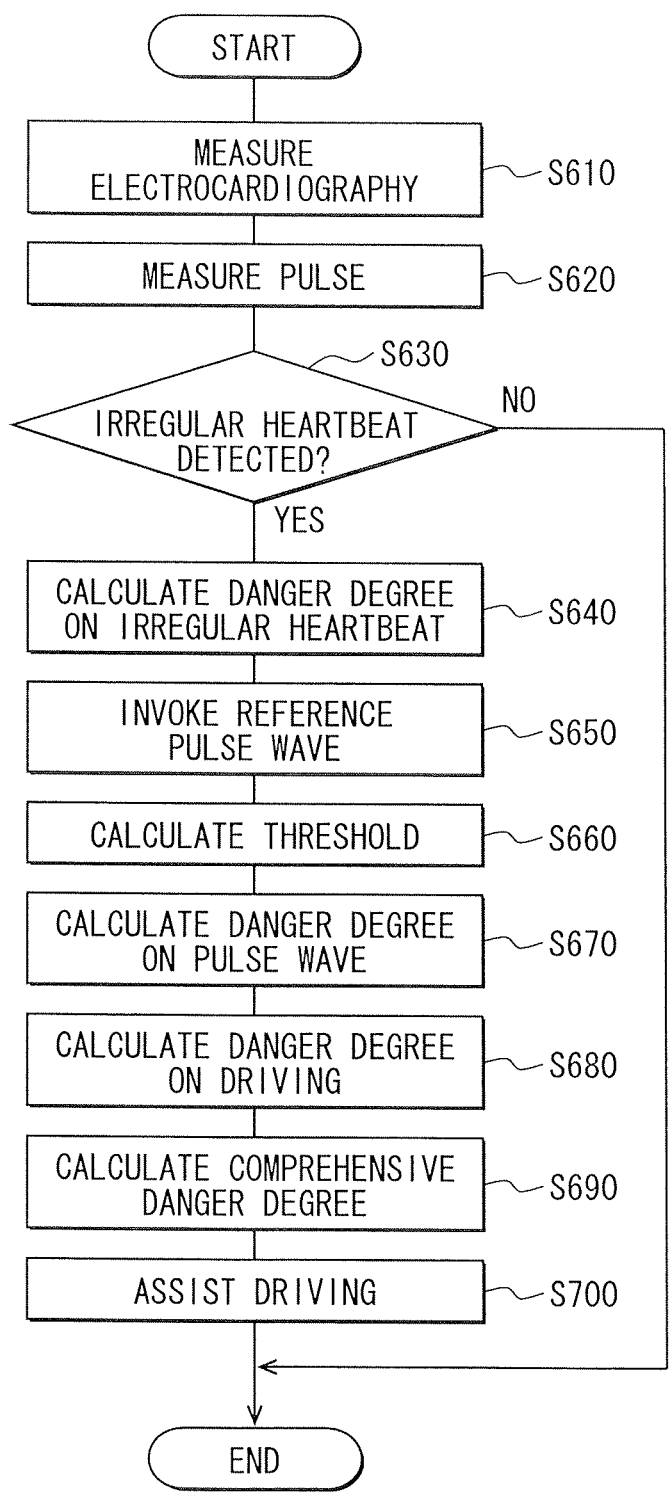
FIG. 14 is a flowchart diagram illustrating a process executed by the living body state monitor apparatus.

The process which the living body state monitor apparatus 1 (in particular, the control circuit 7) executes is explained with reference to FIG. 14. This process is started when the ignition signal of the subject vehicle is inputted into the living body state monitor apparatus 1 and, further, executed repeatedly every predetermined time interval.

S610 to S670 are the same as S10 to S70 in the first embodiment, respectively. At S680, driving information is extracted and the danger degree on driving is calculated from the extracted driving information.

The following is the extracted driving information.
Driving information about method of stop at intersection
Acceleration just before intersection (Navigation information+acceleration)
Velocity just before intersection (Navigation information+velocity)
Driving information about method of travel in straight road
Velocity in straight road (Navigation information+velocity)
Steering angle in straight road (Navigation information+steering angle)

A danger degree on driving (i.e., driving danger degree) is calculated as follows.

When the number of times the steering angle exceeds a threshold value during traveling a straight road within a predetermined time period is greater than a predetermined number, it is determined to be meandering driving, calculating the driving danger degree to be high. When the time period during which the velocity continuously exceeds a threshold value while traveling a straight road is greater than a predetermined value, it is determined to be excessive velocity driving, calculating the driving danger degree to be high.

When the velocity is not less than a threshold value at the time of passing through an intersection, it is determined to be halt disregard, calculating the danger degree to be high. At S690, a comprehensive danger degree is calculated. This comprehensive danger degree is obtained by comprehensively combining the danger degree on irregular heartbeat calculated at S640, the danger degree on pulse wave calculated at S670, and the driving danger degree calculated at S680. For example, the comprehensive danger degree can be obtained by adding up a point calculated based on the danger degree on irregular heartbeat, a point calculated based on the danger degree on pulse wave, and a point calculated based on the driving danger degree.

At S700, a driving operation assistance is executed based on the comprehensive danger degree calculated at S690. For example, when the comprehensive danger degree is in the highest level, a vehicle control is made such as stop, deceleration, prohibition of starting-off. In addition, when the comprehensive danger degree is lower than it, a signal is outputted to an external source via the communication device 9. The outputted signal may include an electrocardiography waveform, a pulse waveform, a comprehensive danger degree, an identification number of the driver or the subject vehicle, for instance. In addition, when the comprehensive danger is further lower, a warning may be executed in a vehicle compartment of the subject vehicle using the display device 29 or the sound output device 31. This warning is more conspicuous as the comprehensive danger degree becomes higher. In addition, when the comprehensive danger degree does not exist or when the comprehensive danger degree is less than a predetermined value, a driving operation assistance is not executed.

According to the living body state monitor apparatus 1 of the present embodiment, the driving danger degree is also taken into consideration based on S680, enabling the more correct determination of the danger degree on driver's living body state. The present invention is not limited to the above mentioned embodiments at all. It can be achieved in various manners within a scope not departing from the present invention.

Figure 15:
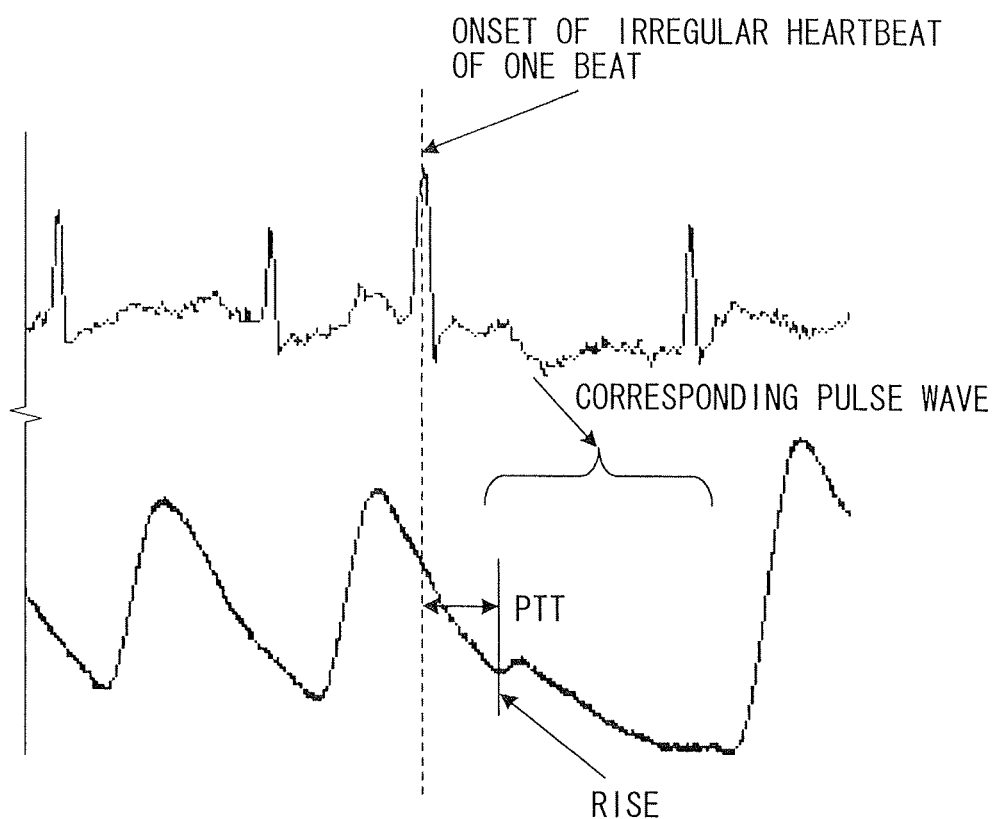
FIG. 15 is a diagram for explaining an example which illustrates a case where there is no pulse wave response to an irregular heartbeat of one beat.

For example, in the living body state monitor apparatus 1 of each of the embodiments, an irregular heartbeat of one beat may be detected as indicated in FIG. 15. When a time period (i.e., PTT: Pulse Transition Time) (i) from the onset time point when an irregular heartbeat occurs (ii) to the rise time point when a peak of a pulse wave rises after the onset of the irregular heartbeat, is greater than a threshold value, it is determined that there is no pulse wave response to the irregular heartbeat of one beat.

In addition, the living body state monitor apparatus 1 of each of the embodiments may amend a pulse wave feature quantity based on driving information. This amendment can be executed, for example, as follows. First, moving object information is acquired using the information acquisition equipment group 5. Such moving object information to be acquired includes an acceleration of the subject vehicle acquired by the acceleration sensor 17, a vehicle velocity detected by the velocity sensor 19, a steering angle of the steering wheel S acquired by the steering angle sensor 21, and a curvature and a vertical interval of a road, which the subject vehicle travels, acquired by the navigation apparatus 23.

Next, an amendment value for information on pulse wave is calculated using the acquired moving object information. That is, the living body state monitor apparatus 1 stores previously an association table or map of the moving object information and the amendment value of the information on pulse wave in the ROM 37; the acquired moving object information is applied to the association table or map, thereby calculating an amendment value for the information on pulse wave.

The meaning for amending the information on pulse wave is as follows. When the subject vehicle is accelerated (horizontally, laterally, or longitudinally), the pulse wave information is varied from an original value because G force is added to the blood. In addition, because the driver's hand and pulse wave sensor 15 move when the steering wheel S is manipulated, the pulse wave information varies from an original value. In order to acquire the original pulse wave information, it is necessary to amend the pulse wave information to cancel the above variation.

Out of the moving object information, an acceleration of the subject vehicle acquired by the acceleration sensor 17, a vehicle velocity detected by the velocity sensor 19, and a curvature and a vertical interval of a road, which the subject vehicle travels, acquired by the navigation apparatus 23 are information that reflects the quantity and direction of the acceleration of the subject vehicle. The variation amount of the pulse wave information produced by the acceleration is determined by the quantity and direction of the acceleration. Thus, from the moving object information mentioned above, the amendment amount for canceling the influence due to the acceleration is computable.

Out of the moving object information, a steering angle of the steering wheel S acquired by the steering angle sensor 21 is information reflecting the movement of the driver's hand and the pulse wave sensor 15. Therefore, the amendment amount for canceling the influence due to the motion of the driver's hand and the pulse wave sensor 15 is computable from the steering angle of the steering wheel S.

The association between the moving object information and the amendment amount can be defined by repeatedly executing tests to measure a variation amount of the pulse wave information while changing an amount of the moving object information. The living body state monitor apparatus 1 can be not only an in-vehicle apparatus but also a medical apparatus arranged in home, a hospital, etc.

In addition, the living body state monitor apparatus 1 may calculate a danger degree on pulse wave based on a variation of a pulse wave feature quantity.

Furthermore, the storage device 43 functions as a living body information storage device to store an irregular heartbeat and a pulse wave feature quantity. Herein, the control circuit 7 functioning as the living body state determination section may determine a danger degree on living body state using a contrast result between (i) a pulse wave feature quantity, which is within a past predetermined time period and stored by the living body information storage device, and (ii) a pulse wave feature quantity extracted by the pulse wave feature quantity extraction section.

In this case, for instance, as the ratio of the pulse wave feature quantity extracted by the pulse wave feature quantity extraction section to the pulse wave feature quantity within the past predetermined time period is great, it can be determined that the danger degree on living body state is high (or low).

Yet further, the control circuit 7 functioning as the living body state determination section may determine a danger degree on living body state by classifying information used for determination into a plurality of classifications, and determining and calculating a danger degree with respect to each of the classifications.

Thus, even if information belonging to one or some of the several classifications has a mistake (e.g., an incorrect detection resulting from noises), the danger degree on living body state can be determined correctly.

It will be obvious to those skilled in the art that various changes may be made in the above-described embodiments of the present invention. However, the scope of the present invention should be determined by the following claims.

What is claimed:

1. A living body state monitor apparatus comprising:
    a living body information acquisition device to acquire living body information containing an electrocardiography waveform and a pulse waveform with respect to a living body of a user;
    an irregular heartbeat detection section to detect an irregular heartbeat from the electrocardiography waveform;
    a pulse wave feature quantity extraction section to extract a pulse wave feature quantity from a pulse wave corresponding to the irregular heartbeat;
    a living body state determination section to determine a danger degree on living body state of the user using both first information and second information,
        the first information being at least one of information on kind of an irregular heartbeat detected by the irregular heartbeat detection section and information on time of the irregular heartbeat,
        the second information being at least one of a pulse wave feature quantity extracted by the pulse wave feature quantity extraction section, and a variation of the extracted pulse wave feature quantity; and
    a living body information storage device to store an irregular heartbeat and a pulse wave feature quantity,
    wherein the living body state determination section determines a danger degree on living body state using a contrast result between (i) a pulse wave feature quantity, which is within a past predetermined time period and stored by the living body information storage device, and (ii) a pulse wave feature quantity extracted by the pulse wave feature quantity extraction section.

2. The living body state monitor apparatus according to claim 1, wherein the pulse wave feature quantity includes at least one of:
    (i) a maximum value in the pulse wave of one peak corresponding to the irregular heartbeat;
    (ii) a minimum value in the pulse wave of one peak corresponding to the irregular heartbeat;
    (iii) an amplitude in the pulse wave of one peak corresponding to the irregular heartbeat;
    (iv) a rise time in the pulse wave of one peak corresponding to the irregular heartbeat;
    (v) a time interval in between a first rise of the pulse wave of one peak corresponding to the irregular heartbeat and a second rise preceding the first rise by one peak;
    (vi) a maximum value in the pulse wave having (a) peaks within a predetermined time period corresponding to the irregular heartbeat, or (b) peaks whose number is a predetermined number corresponding to the irregular heartbeat;
    (vii) a minimum value in the pulse wave having (a) peaks within a predetermined time period corresponding to the irregular heartbeat, or (b) peaks whose number is a predetermined number corresponding to the irregular heartbeat;
    (viii) an average amplitude in the pulse wave having (a) peaks within a predetermined time period corresponding to the irregular heartbeat, or (b) peaks whose number is a predetermined number corresponding to the irregular heartbeat;
    (ix) an average rise time in the pulse wave having (a) peaks within a predetermined time period corresponding to the irregular heartbeat, or (b) peaks whose number is a predetermined number corresponding to the irregular heartbeat;
    (x) an average pulse interval in the pulse wave having (a) peaks within a predetermined time period corresponding to the irregular heartbeat, or (b) peaks whose number is a predetermined number corresponding to the irregular heartbeat;

(xi) a variation of amplitudes in the pulse wave having (a) peaks within a predetermined time period corresponding to the irregular heartbeat, or (b) peaks whose number is a predetermined number corresponding to the irregular heartbeat; and (xii) a variation of pulse intervals in the pulse wave having (a) peaks within a predetermined time period corresponding to the irregular heartbeat, or (b) peaks whose number is a predetermined number corresponding to the irregular heartbeat.

3. The living body state monitor apparatus according to claim 1, further comprising:

a personal information storage device to store personal information containing information on irregular heartbeat and/or previous illness, the personal information being previously inputted or previously detected for each individual, wherein the living body state determination section uses the personal information stored in the personal information storage device when determining the danger degree on living body state.

4. The living body state monitor apparatus according to claim 1, wherein:

the irregular heartbeat detection section detects an electrocardiography feature quantity from the electrocardiography waveform; and the living body state determination section uses the electrocardiography feature quantity or a variation of the electrocardiography feature quantity when determining the danger degree on living body state.

5. The living body state monitor apparatus according to claim 1, wherein the living body state determination section changes a pulse wave feature quantity and a determination method, which are used for determining the danger degree on living body state, according to kinds of the irregular heartbeat.

6. The living body state monitor apparatus according to claim 1, wherein:

the living body state determination section detects an irregular heartbeat of one beat; and the living body state determination section determines that there is no pulse wave response to the irregular heartbeat of one beat in cases where a time period from an onset of the detected irregular heartbeat up to a rise of a pulse wave, which arises for a first time after the onset of the irregular heartbeat, is greater than a threshold value.

7. The living body state monitor apparatus according to claim 1, being mounted in a vehicle and further comprising:

a driving information acquisition section to acquire driving information containing, at least one of a vehicle velocity, a vehicle acceleration, a steering angle, and a navigation, wherein the living body state determination section uses the driving information when determining the danger degree on living body state.

8. The living body state monitor apparatus according to claim 7, wherein the living body state determination section amends the pulse wave feature quantity based on the driving information.

9. The living body state monitor apparatus according to claim 1, further comprising:

an output device to output a determination result of the living body state determination section to an external source.

10. The living body state monitor apparatus according to claim 1, further comprising:

a warning device to execute a warning according to a determination result of the living body state determination section.

11. The living body state monitor apparatus according to claim 1, further comprising:

an assistance device to execute an assistance according to a determination result of the living body state determination section.

12. The living body state monitor apparatus according to claim 1, wherein the living body state determination section determines a danger degree on living body state by classifying information used for determination into a plurality of classifications, and determining and calculating a danger degree with respect to each of the classifications.

13. A living body state monitor apparatus comprising:

a living body information acquisition device to acquire living body information containing an electrocardiography waveform and a pulse waveform with respect to a living body of a user;

an irregular heartbeat detection section to detect an irregular heartbeat from the electrocardiography waveform;

a pulse wave feature quantity extraction section to extract a pulse wave feature quantity from a pulse wave corresponding to the irregular heartbeat;

a living body state determination section to determine a danger degree on living body state of the user using both first information and second information, the first information being at least one of information on kind of an irregular heartbeat detected by the irregular heartbeat detection section and information on time of the irregular heartbeat, the second information being at least one of a pulse wave feature quantity extracted by the pulse wave feature quantity extraction section, and a variation of the extracted pulse wave feature quantity, wherein the living body state determination section changes a pulse wave feature quantity and a determination method, which are used for determining the danger degree on living body state, according to kinds of the irregular heartbeat.

14. A living body state monitor apparatus comprising:

a living body information acquisition device to acquire living body information containing an electrocardiography waveform and a pulse waveform with respect to a living body of a user;

an irregular heartbeat detection section to detect an irregular heartbeat from the electrocardiography waveform;

a pulse wave feature quantity extraction section to extract a pulse wave feature quantity from a pulse wave corresponding to the irregular heartbeat; and a living body state determination section to determine a danger degree on living body state of the user using both first information and second information, the first information being at least one of information on kind of an irregular heartbeat detected by the irregular heartbeat detection section and information on time of the irregular heartbeat, the second information being at least one of a pulse wave feature quantity extracted by the pulse wave feature quantity extraction section, and a variation of the extracted pulse wave feature quantity, wherein the living body state determination section detects an irregular heartbeat of one beat; and the living body state determination section determines that there is no pulse wave response to the irregular heartbeat of one beat in cases where a time period from an onset of the detected irregular heartbeat up to a rise of a pulse wave, which arises for a first time after the onset of the irregular heartbeat, is greater than a threshold value.

15. A living body state monitor apparatus being mounted on a vehicle and comprising:

- a living body information acquisition device to acquire living body information containing an electrocardiography waveform and a pulse waveform with respect to a living body of a user;
- an irregular heartbeat detection section to detect an irregular heartbeat from the electrocardiography waveform;
- a pulse wave feature quantity extraction section to extract a pulse wave feature quantity from a pulse wave corresponding to the irregular heartbeat;
- a living body state determination section to determine a danger degree on living body state of the user using both first information and second information,
    - the first information being at least one of information on kind of an irregular heartbeat detected by the irregular heartbeat detection section and information on time of the irregular heartbeat,
    - the second information being at least one of a pulse wave feature quantity extracted by the pulse wave feature quantity extraction section, and a variation of the extracted pulse wave feature quantity; and
- a driving information acquisition section to acquire driving information containing, at least one of a vehicle velocity, a vehicle acceleration, a steering angle, and a navigation, wherein the living body state determination section uses the driving information when determining the danger degree on living body state, and the living body state determination section amends the pulse wave feature quantity based on the driving information.

* * * * *